United States Defensive Publication [19] (H) [11] T103,205

Cruickshank [43] Jul. 5, 1983

[54] INTERMEDIATES AND PROCESS FOR INSECTICIDAL 4-PHENYL-2-INDANYL ESTERS

[76] Inventor: Philip A. Cruickshank, 211 Dodds La., Princeton, N.J. 08540

[21] Appl. No.: 407,230

[22] Filed: Aug. 11, 1982

Related U.S. Application Data

[63] Continuation of Ser. No. 286,309, Jul. 24, 1981, abandoned.

[51] Int. Cl.[3] ..... C07C 67/317

[52] U.S. Cl. ..... 560/124

[57] ABSTRACT

Compounds of formulae II, III and IV:

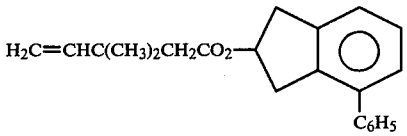

II

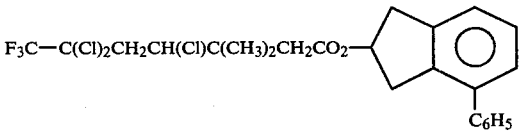

III

-continued

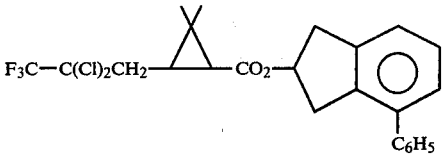

IV are useful intermediates for preparation of an insecticidal compound of formula (I):

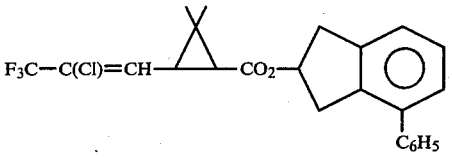

I

The intermediate II is prepared by reacting the acid halide, alkali metal salt, or lower alkyl ester of 3,3-dimethyl-4-pentenoic acid with a compound of the formula

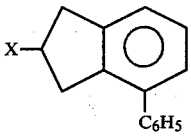

in which X is a hydroxy group or a leaving group.

Intermediate III is prepared by reacting II with 1,1,1-trichloro-2,2,2-trifluoroethane in the presence of a solvent, a solvating agent, and a catalyst. Intermediate III is then di-dehydrochlorinated in the presence of base, in one or two steps, to produce I.

10 Claims, No Sheets Drawing,

21 Pages Specification

The file of this unexamined application may be inspected and copies thereof may be purchased (849 O.G. 1221, Apr. 9, 1968).